United States Patent [19]

Phillips et al.

[11] Patent Number: 4,616,927
[45] Date of Patent: Oct. 14, 1986

[54] SAMPLE CELL FOR LIGHT SCATTERING MEASUREMENTS

[75] Inventors: Steven D. Phillips, Goleta; Jeffrey M. Reece; Philip J. Wyatt, both of Santa Barbara, all of Calif.

[73] Assignee: Wyatt Technology Corporation, Santa Barbara, Calif.

[21] Appl. No.: 671,181

[22] Filed: Nov. 15, 1984

[51] Int. Cl.$^4$ ............................................. G01N 21/00
[52] U.S. Cl. .................................... 356/338; 356/342; 356/343
[58] Field of Search ................ 356/338, 336, 342–343; 250/574

[56] References Cited

U.S. PATENT DOCUMENTS

| | | | |
|---|---|---|---|
| 3,705,771 | 12/1972 | Friedman et al. | 356/342 |
| 4,105,334 | 8/1978 | Halko et al. | 356/70 |
| 4,541,719 | 9/1985 | Wyatt | 356/343 |

OTHER PUBLICATIONS

"Evidence of Mode-Mode Coupling and Nonlocal Shear Viscosity in a Binary Mixture Near the Consolute Point", Lai et al, *Physical Review Letters*, vol. 29, #7, pp. 401–404, 1972.

"Translational and Rotational diffusion Constants of Tobacco Mosaic Virus from Rayleigh Linewidths", Cummins et al. *Biophysical Journal*, vol. 9, 1969, 518–546.

*Primary Examiner*—R. A. Rosenberger
*Assistant Examiner*—Crystal D. Cooper

[57] ABSTRACT

A sample cell is described that permits the measurement of the light scattering properties of very small liquid-borne samples with negligible background interference form the illumination source. A technique is described whereby the cell construction permits the measurement of the illumination intensity at the scattering sample itself, permitting, thereby, the normalization of each detected scattered signal. The cell structure and detection method incorporated therein also permit measurement of extremely small angle scattered intensities without interference of the incident light beam itself.

20 Claims, 5 Drawing Figures

SAMPLE CELL FOR LIGHT SCATTERING MEASUREMENTS

Some of the developments and studies associated with this invention were performed under Contract #DAMD17-84-C-4155 from the U.S. Army Medical Research & Development Command. The Government has certain non-exclusive rights under the terms of this contract.

CO-PENDING APPLICATIONS

The present invention is a new type of light scattering cell and as such will find broad utility in various fields of light scattering determinations. Among some of the most important are those of the type discussed at length in the co-pending applications by some of the inventors of the present cell and technique, namely:

U.S. Pat. No.: 4,490,042
Title: Method for Determining the Properties of Wine
Inventor: Philip J. Wyatt
Date of Filing: June 4, 1981
Date of Issue: Dec. 25, 1984
Art Unit Number: 257

U.S. Pat. No.: 4,541,719
Title: Method and Apparatus for Characterizing Microparticles and Measuring Their Response to Their Environment
Inventor: Philip J. Wyatt
Date of Filing: June 20, 1982
Date of Issue: Sept. 17, 1985
Art Unit Number: 255

U.S. Pat. No.: 4,548,500
Title: Process and Apparatus for Identifying or Characterizing Small Particles
Inventor: Philip J. Wyatt and Gregory M. Quist
Date of Filing: June 22, 1982
Date of Issue: Oct. 22, 1985
Art Unit Number: 255

U.S. patent application Ser. No. 668,711
Title: Method and Apparatus for Measuring the Light Scattering Properties of Small Particles
Inventors: Philip J. Wyatt and Steven D. Phillips
Date of Submission: Nov. 5, 1984.

DEFINITIONS

The term "light" shall mean electromagnetic radiation, either monochromatic or of a broader frequency range, either unpolarized or polarized.

The term "size parameter" shall mean $\rho$, where $\rho = 2\pi a/\lambda$, a is the mean particle radius, and $\lambda$ is the wavelength of the incident electromagnetic radiation in the medium in which the particles are measured.

The term "very small particle" shall mean any particle whose size parameter is less than one.

The term "small particle" shall mean any particle whose size parameter is less than six.

The term "large particle" shall mean a particle whose size parameter is greater than six.

The term "beam" shall mean light propagating in a parallel or nearly parallel direction.

The term "beam diameter" of an incident light source, with a Gaussian intensity profile, such as a laser, shall refer to the diameter of the beam measured between the points at which the intensity has fallen to $1/e^2$ the intensity at the center of the beam.

The team "forward scattering direction" shall mean all rays, i.e. directed line segments, propagating at an angle less than 90 degrees with respect to the direction of the incident beam.

The term "backward scattering direction" shall mean all rays, i.e. directed line segments, propagating at an angle greater than 90 degrees with respect to the direction of the incident beam.

For plane polarized light, the plane perpendicular to the direction of the wave's electric field is called the V-plane and said plane polarized light is vertically polarized with respect to said perpendicular plane. The corresponding H-plane is perpendicular to the V-plane and contains the incident wave's electric field.

The terms "background effects" and "background contributions" shall mean any source of light detected by an instrument which is not due to the scattering of light from the sample. We will be concerned solely with background contributions arising from interactions of the incident beam with the sample cell and related apparatus. We will assume any background produced by light scattering from a pure solvent itself is negligible.

SUMMARY OF THE INVENTION

A new type of cell is disclosed for making light scattering measurements on very small liquid samples. The preferred embodiment of the invention comprises a right cylinder with a hole bored through a diameter. The cylinder and hole are optically polished and the cylinder is surrounded by an array of detectors lying in the plane of the hole and parallel to the base. Means are provided for introducing and removing a particle-bearing sample fluid. The sample introduced into the hole, thereby, is illuminated by a collimated light beam whose diameter is much smaller than the diameter of the hole. This beam passes directly through the hole and enters and leaves the cell by means of special windows mounted externally to the cell. Because of the the slight difference of refractive index between the fluid and the surrounding glass cell, very little stray or background light enters the detectors, even at very small scattering angles. The invention also provides means for attenuating small angle scattered intensities which are a source of detector saturation in conventional light scattering instruments. Other cell structures are disclosed together with a novel method for normalizing the detected scattered intensities to the incident beam intensity.

BACKGROUND

Many important laboratory and industrial programs are involved with the measurement of fine particles in suspension by light scattering techniques. Foremost among them is the light scattering procedure for the determination of molecular weights of unknown solutes suspended in various types of solvents. Without going into the details of this procedure, which is described in many texts such as Kerker's book *The Scattering of Light and Other Electromagnetic Radiation*, the general measurement involves the preparation of a suspension of the unknown material followed by its illumination by a collimated beam of monochromatic light. The intensity of the light scattered by the suspension is then measured as a function of angle and solute concentration. Since the scattering properties of the sample cell or cuvette containing the solution may interfere with this determination, it is important to use a cell whose so-called "background" contributions will be minimal and affect the determinations least. Ideally, the cell will permit the measurement of the scattering properties of the solute particles or molecules at increasingly lower concentrations.

Many types of assays and bioassays, such as described by Wyatt in his two co-pending applications cited above or his chapter in the book edited by Charalambous entitled *Analysis of Foods and Beverages*, involve the preparation of aqueous suspensions. Subsequent measurement of these suspensions by light scattering means involves detecting very small changes in the measured light scattering properties of the solutions. Often, the accuracy of the results will be affected by background effects created by the scattering cell itself. Even the very simplest determinations of transmission or optical density, such as performed by conventional spectrophotometers of the type manufactured by Bausch and Lomb, depend critically on the background contributions of the liquid-containing cell. Furthermore, some compounds, such as those separated by means of liquid chromatography, are obtained in such small volumes that the cell containing them also must have a very small volume, typically on the order of microliters or less. Thus, "background" effects become increasingly important because of the close proximity of the sample cell liquid and air interfaces to the field of view of the detection system.

While studying many of the aforementioned measurements, we have discovered a cell structure and method of measurement that permits the examination by light scattering means of extremely small volumes of liquid-borne samples at virtually all scattering angles, no matter how small, without introducing significant background artifacts from the containing sample cell itself. This cell structure permits, in addition, the determination of the actual light flux incident upon the sample being examined, an often important requirement for many light scattering applications.

DETAILS OF THE INVENTION

Figure 1:
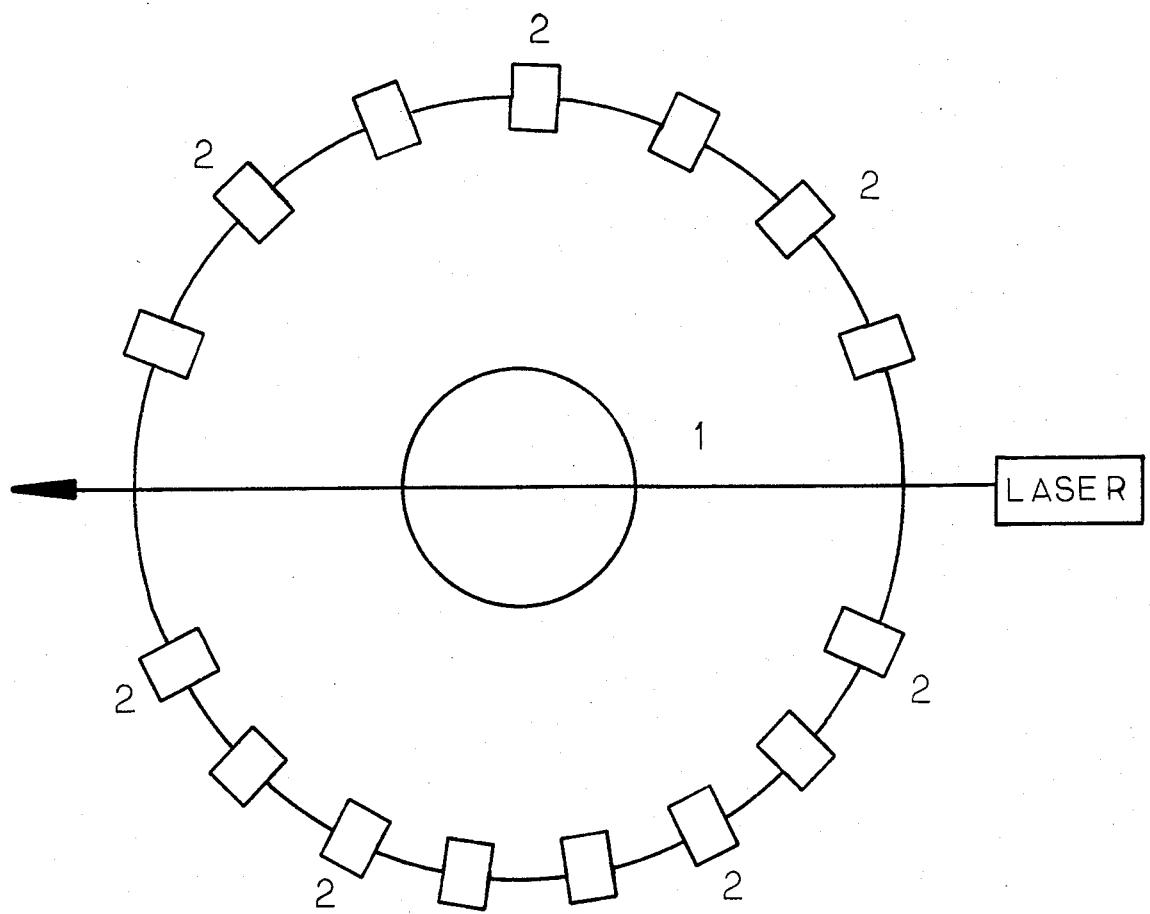
FIG. 1 shows a top view of a cylindrical scattering cell surrounded by a set of collimated detectors and illuminated by a collimated light beam.

A typical detection system is shown in FIG. 1. An incident light source, usually a monochromatic beam 1 such as produced by a laser passes through the sample cell. Also shown in this figure is a set of discrete detectors 2 spaced circumferentially about this cell. Each detector is collimated so that its field of view includes only a very small volume at the center of the cell.

Figure 2:
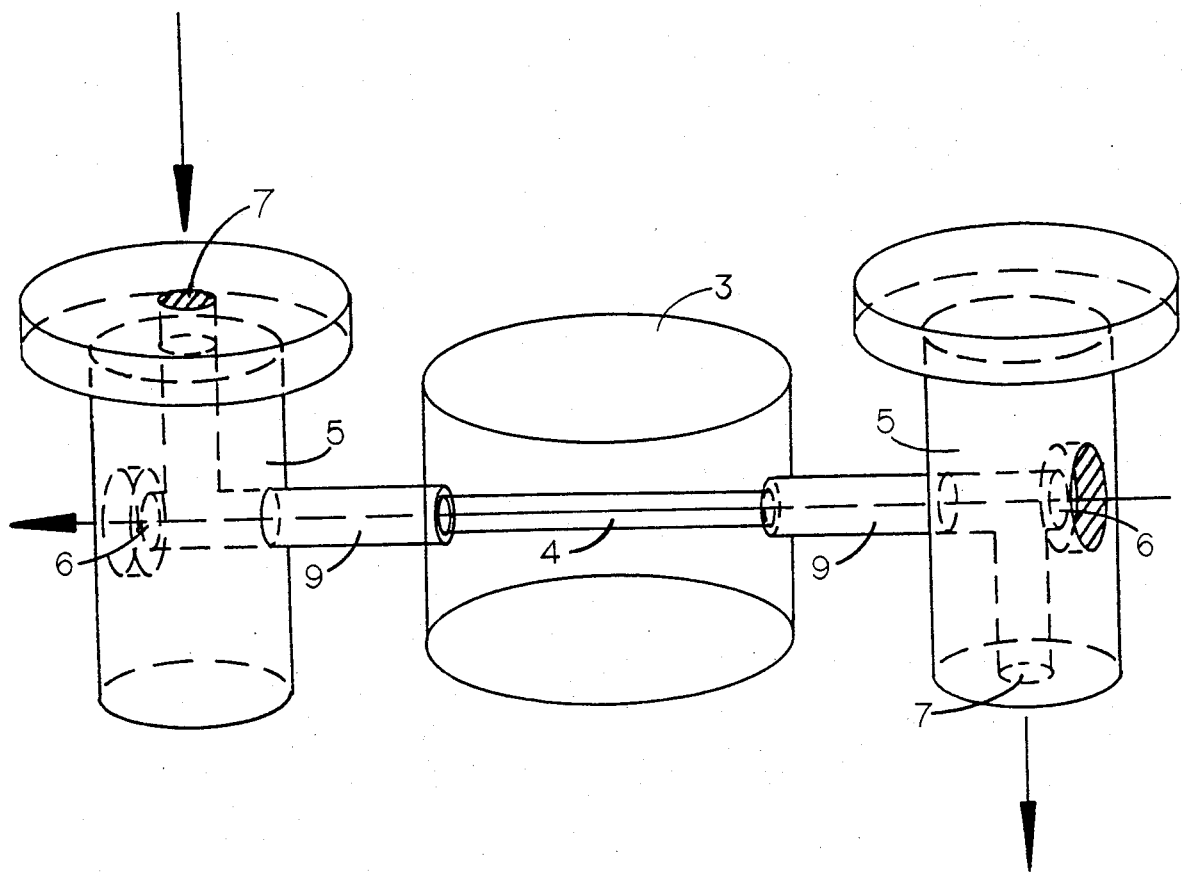
FIG. 2 presents a perspective view of a preferred embodiment of the scattering cell showing the illumination source, the flow channel, the cell windows, and the fittings for introducing samples.

FIG. 2 presents a perspective view of the scattering cell of the preferred embodiment of our invention. It consists of a cylinder 3 of glass or other transparent material of refractive index generally chosen close to the index of the solvent carrying the sample. Through the cylinder, a hole 4 is drilled along a diameter of the cylinder and lying in the plane of the detector array. The outer diameter of the cylinder and the hole interior surfaces are optically polished to remove any surface irregularities. Attached to each aperture of the cylinder is a fixture 5 containing an optical window 6 and a bore 7 to carry the sample into or out of the cell.

Figure 3:
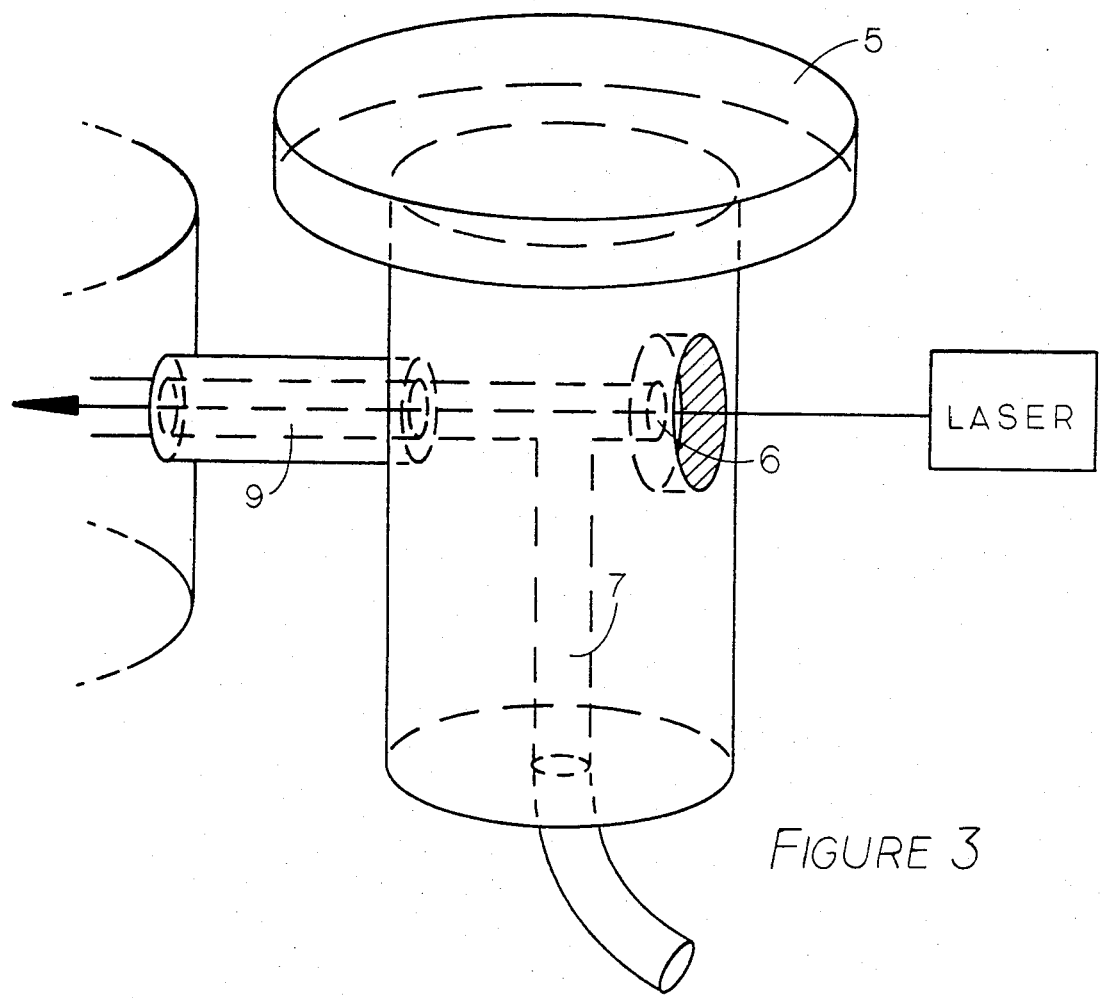
FIG. 3 shows a flow fixture that is attached to the cylindrical sample cell to carry liquid-borne samples into or out of it.

FIG. 3 shows a greater detail of the fixtures 5 which, in the preferred embodiment of this invention, contains a tube 9 to convey the liquid-borne sample into or out of the cell hole 4. Note that the light beam that passes through the cell must, in the preferred embodiment of this invention, be of even smaller cross section than the hole 4. A typical cell would have a hole diameter of 2.0 mm and be illuminated with a laser beam diameter of 0.4 mm such as is produced by a special He-Ne laser manufactured by Melles Griot. As should be evident from FIGS. 1-3, were the refractive index of the cylinder the same as the refractive index of the liquid passing through the cell, the set-up would correspond to the geometry of the large radius of curvature structure of FIG. 1; yet the beam passing through the cell of the present invention does not strike any surface within the field of view of any detector. As seen in FIG. 2, the beam entrance and exit windows 6 are far removed from the center of the cell, which eliminates the background contributions associated with the beam traversing an air/glass/liquid interface. In addition, the sample volume contained within this cell is extremely small relative to the volume required for the traditional cell of such large radius of curvature. The actual volume of the same would depend on the diameter of the hole 4 cut into the cylinder. Light scattered from this small sample volume will not be attenuated significantly as it passes through the glass cell region to the detectors. This also permits the examination of samples of greater particle density without the usual multiple scattering degradations that would be caused by the intervening particles in a comparably sized scattering cell, i.e. a cell where the glass region of the present invention were replaced by an additional liquid sample.

The difference of refractive index between the solvent fluid passing through hole 4 and that of the glass cylindrical cell 3 surrounding it results in another important feature of our invention. We have already stated that these refractive indices will be quite close. As long as they are different, it will be possible to obtain measurements of light scattered at very small angles by particles or molecules illuminated by the highly collimated light source with negligible background contributions, as shall soon be demonstrated. Typically, the refractive index of the liquid $n_1$ will be that of water, 4/3, while that of the glass $n_2$ will be about 3/2. Applying Snell's Law (see FIG. 4) to determine the refraction of a ray 1 striking the water-glass interface 8 at an angle $\theta$ yields the result $$n_1 \sin\left(\frac{\pi}{2} - \theta\right) = n_2 \sin\left(\frac{\pi}{2} - \theta'\right), \tag{1}$$

where the angle of incidence is $\pi/2-\theta$ and the angle of refraction is $\pi/2-\theta'$. Expanding the sine functions in Eq. (1) and collecting terms, immediately results in $$n_2 \cos \theta' = n_1 \cos \theta, \quad (2)$$

Note that point 9, for the case of the scattering cell of the preferred embodiment, lies ahead, i.e. to the left, of the center of the cell 10, and is on the interface. A detector means detecting light at an angle $\theta'$ would be collimated to be centered on point 10.

It is interesting to note that as the scattering angle $\theta$ becomes very small, i.e. approaches zero, the source of the scattering event 11 whose refracted rays are detected at $\theta'$ moves to the right of the center of the cell 10. In the limit at $\theta = 0$, $\theta' = \cos^{-1}(8/9) = 27.27°$. Thus, no matter how small the scattering angle $\theta$, the refracted ray will be detected at an angle $\theta'$ sufficiently distant from all interfaces to permit said detector means to avoid receiving any direct contributions from the incident beam 1.

Figure 4:
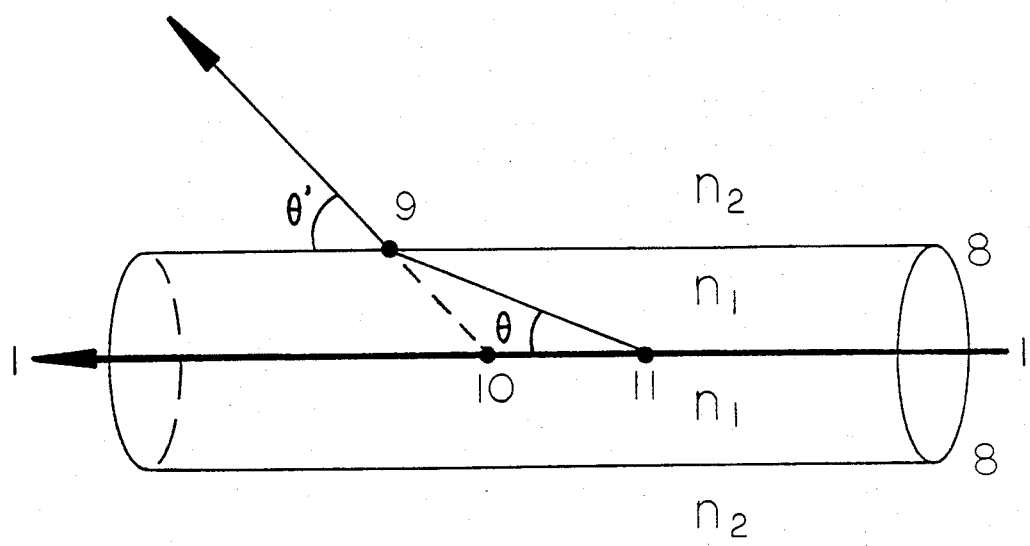
FIG. 4 shows the application of Snell's Law at the interface between two media.

The scattering angle $\theta$ of FIG. 4 represents the most important independent variable of a light scattering measurement. Accordingly, in the preferred embodiment of our invention, the detector means 2 of FIG. 1 should be placed so that there is a one-to-one correspondence with the set of $\theta$-angles selected for an experiment. An often used set of scattering angles $\theta$ is selected such that the angles are equally spaced in $\sin \theta/2$. The latter choice is particularly convenient for certain types of measurements related to molecular weight determinations or small particles whose refractive indices are very close to that of the medium surrounding them. If the detectors surrounding the glass cell were spaced equidistantly in $\theta'$ or in $\theta'/2$, the interpretation of the date so-detected in terms of the physically important scattering angle $\theta$ would require the complex mathematical inversion of Eq. (1) for each measurement. Instead, in a preferred embodiment of our invention, we place the detector means about the cell at those angles $\theta'_i$ that correspond to the selected set of scattering angles $\theta_i$. For example, for equidistant spacing in $\sin \theta/2$ such that $$0.2 \leq \sin \theta/2 \leq 0.9, \quad (3)$$

which is a range frequently found in scattering measurements, Eq. (1) may be solved for $\theta'$ in terms of $\sin \theta/2$ as follows:

$$n_2 \cos \theta' = n_1 \cos \theta = n_1(1 - 2 \sin^2 \theta/2). \quad (4)$$

Hence $$\theta' = \cos^{-1}\left[\frac{n_1}{n_2}(1 - 2 \sin^2 \theta/2)\right]. \quad (5)$$

For a typical case where the cell is optical glass of refractive index 3/2 and the sample is in a liquid of refractive index 4/3, a set of discrete detectors at angle $\theta'_i$ would be placed according to the transformation table below:

| Table of Transformed Scattering Angles | | |
|---|---|---|
| $\sin \theta i/2$ | $\theta i$ | $\theta' i$ |
| .2 | 23.07 | 35.13 |
| .25 | 28.96 | 38.95 |
| .3 | 34.92 | 43.21 |
| .35 | 40.97 | 47.84 |
| .4 | 47.16 | 52.81 |
| .45 | 53.49 | 58.07 |
| .5 | 60.00 | 63.61 |
| .55 | 66.73 | 69.44 |
| .6 | 73.74 | 75.59 |
| .65 | 81.08 | 82.08 |
| .7 | 88.85 | 88.98 |
| .75 | 97.18 | 96.38 |
| .8 | 106.26 | 104.41 |
| .85 | 116.42 | 113.30 |
| .9 | 128.32 | 123.45 |

To make a measurement at a very small scattering angle in the forward direction will require a very precise placement and collimation of the detector means, since refraction causes a small range of $\theta'$ values to correspond to a larger range of $\theta$-values, for $\theta$ near 0°. For a measurement at, say, $\theta = 5.73°$, the detector means would have to be placed at 27.82°, a scant 30' of arc from the limiting $\theta = 0°$ value, where $\theta' = 27.27°$. Nevertheless, light scattered in this direction may be precisely intercepted by the carefully set detector means.

As the average particle size parameter $\rho$ becomes larger, the relative intensity of light scattered in the forward direction to that scattered into the backward direction becomes very large. For many types of instruments detecting scattered light at small angles, this becomes a troublesome problem as large forward scattering contributions may overwhelm and saturate the detector means monitoring forward scattering events. This is not true for our invention because of the unique attenuation of such forward scattering light. As $\theta \to 0$, the fraction of scattered light flux refracting into angle $\theta'$ becomes progressively smaller and becomes zero when $\theta = 0$. In FIG. 4, the fraction of scattered light flux reflected at the water glass interface 8 in terms of the angle of incidence, $\theta$, may be determined from Fresnel's relations discussed, for example, in the textbook *Light* by R. W. Ditchburn. For the case of vertically polarized incident light, the reflected fraction $\rho_w$ from liquid to glass is given by the relation $$\rho_w = \frac{\sin^2(\theta' - \theta)}{\sin^2(\theta' + \theta)} \quad (6)$$

where $\theta$ is given by Eq. (2). Note that as $\theta \to 0$, $\rho_w \to 1$, i.e. most of the light is reflected and only a decreasing fraction $1 - \rho_w$ is refracted into the small angle detector means. In the case of normal incidence $\theta$ and $\theta' = \pi/2$. Taking this limiting case and applying Snell's law, we obtain $$\rho_{w90°} = \frac{(n_1 - n_2)^2}{(n_1 + n_2)^2} = \frac{(1/6)^2}{(17/6)^2} = 0.34\% \quad (7)$$

Thus by placing the scattering particles in a medium of refractive index *less* than that of the surrounding scattering cell, which is a natural procedure whenever particles are measured in solution, our invention permits the detection of light scattered at small angles without saturating the small angle detector means.

Although we have explained the key elements of our invention by means of a preferred cylindrical embodiment discussed above, it will be clear to those skilled in the art of light scattering that our invention applies equally to many other geometries and cell structures. The latter is of particular significance as it represents the hydrosol equivalent of the single particle aerosol particle analyser disclosed in the co-pending application by Wyatt and Phillips. Highly irregular particles will scatter light as a complex function of both the polar angle $\theta$ and the azimuthal angle $\phi$. The variation of intensity with $\phi$ at a fixed $\theta$ for a spherically symmetric particle, on the other hand, is a simple function of $\cos^2 \phi$ and $\sin^2 \phi$. The detection, classification, and measurement of particles of complex structure requires, therefore, that measurements be performed at many $(\theta, \phi)$ locations that do not lie in a plane. If the incident light be plane polarized vertically with respect to a set of detectors lying along a great circle of the sphere/air interface, then there is another great circle at right angles to this with respect to which the incident light is horizontally polarized. Further details of the detection geometries are discussed in the co-pending cited Wyatt and Phillip's application. The measurement and classification of such particles from the collected light scattering data are discussed in the co-pending application by Wyatt and Quist. Note also that a sphere is not the only three dimensional structure for which our invention will apply, though it certainly provides the greatest flexibility for scattering measurements. Other useful three dimensional structures include cubes and many regular and irregular polyhedra.

It is interesting to note that the transformed detector locations discussed above for the cylindrical cell embodiment of our invention apply equally well to a spherical cell. The angle of incidence of the scattered ray depends only on $\theta$ insofar as the application of Snell's law is concerned and is independent of $\phi$. The azimuthal scattering angles $\phi$ would be selected to define different sets of detectors, each lying on a great circle, as described by Wyatt and Phillips.

It should be noted that the hole 4 through the cell can contain additional structures such as a small spherical cavity at the center of the cell. This cavity would allow scattered light originating at the center of the cell to proceed along a radial line out of the cell and into the detectors. This would eliminate the refraction problem at the liquid/glass interface arising from the non-perpendicularity of the scattered ray at the interface. Hence, all detectors, except those whose field of view is obscured by hole 4, will be simultaneously viewing the center of the cavity. Such an arrangement would be important when, for example, viewing a single particle is desired, which requires many detectors viewing the same particle at the same location at the same time. The spherical cavity within the spherical cell could be easily fabricated, for example, by assembling the spherical cell from two hemispheres ground on a lens grinding machine. After cutting a sample introduction channel in each hemisphere and a central hemispherical cavity in each hemisphere, the two hemispheres and cavities would be polished and joined together by index matching cement.

Figure 5:
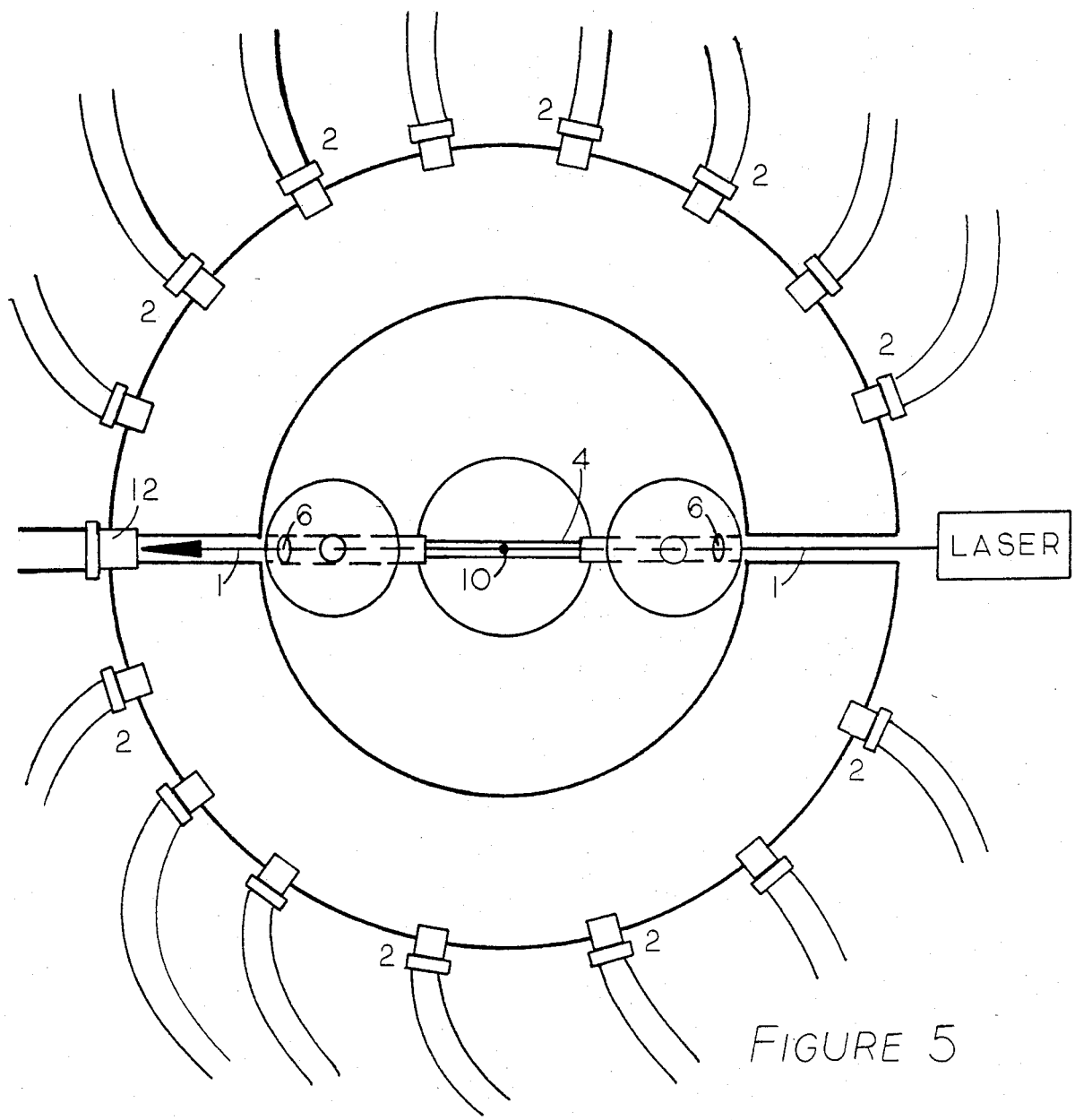
FIG. 5 is a top view of a preferred embodiment showing the sample cell, the normalization beam monitor, several typical detector means, and the illumination source.

FIG. 5 shows a perspective view of the assembled cell complete with fixtures and surrounded with an array of detectors. Consider the beam monitor 12. It will monitor the beam intensity after passing through the sample. If n is the number of particles per ml and $\sigma$ is the average scattering cross section per particle, then in a path length X, the intensity I of the illumination source will be attenuated according to Beer's Law as:

$$I = I_o \exp-(n\sigma X), \tag{8}$$

where, $I_O$=the incident intensity. For many types of measurements, it is important that the scattered intensities detected be normalized to the intensity of the illumination incident upon the scattering particles. This normalization is particularly important in the measurement of molecular weights or monitoring critical growth processes. Some instruments split the incident beam and use the fraction removed thereby as this normalization factor $I_O$. However, this value, so-obtained, may not well present the actual intensity at the sample because of the attenuation of the intervening sample and reflections at the cell interfaces. Furthermore, this attenuation will vary from sample to sample. By introducing a beam monitor such as shown in FIG. 5, we are able to obtain very accurate representations of the normalized scattered intensities as follows.

Consider that the total sample path through the cell hole 4 is 2X and that the detectors 2 are collimated to view only the small volume at the center of the hole, a distance X from the beam entrance window 6 in FIG. 5. The intensity at the beam monitor 12 relative to the incident intensity at the entrance window is given by application of Beer's Law with the incorporation of the Fresnel reflection fraction f, at each air-glass interface and Fresnel reflection fraction g at each glass/liquid interface. Hence, the total reflection fraction is $F = f + g - fg$ whence:

$$I_2 = I_o(1-F)^2 \exp-(2n\sigma X). \tag{9}$$

The intensity at the center of the sample, $I_1$, on the other hand, is just $$I_1 = I_o(1-f) \exp-(n\sigma X). \tag{10}$$

Instead of normalizing the scattered intensities by $I_o$, we should normalize by the factor of $I_1$ of Eq. (10). However, the normalization factor $$N \equiv I_1 = I_o(1-F)\exp-(n\sigma X), \tag{11}$$

$$= \sqrt{I_o}\ \sqrt{I_2}\ .$$

Furthermore, any normalization factor which is proportional to N is an equally suitable normalization factor. We are only concerned with the relative intensity at the center of the cell which varies from sample-to-sample due to differences in turbidities and from time-to-time due to the time varying intensity of the light source.

$$\text{Let } N_2 = \sqrt{I_3}\ \sqrt{I_2} \tag{12}$$
$$\text{where } I_3 = K I_o,\ 0 < K < 1$$

Hence, by monitoring a small fraction, K, of the incident source intensity 13 and monitoring $I_2$ at the beam monitor 12, one obtains $N_2$ via Eq. (12). The value of K need not be known as $N_2$ is only a relative normalization factor.

This final normalization obtained as the square root of the product of relative intensities at the beam monitor 12 and an external monitor 13 represents, therefore, the optimum normalization constant since it is always proportional to the real time value at the sample.

While there has hereinbefore been presented what is at present considered to be the preferred embodiment and process of our invention which has described a scattering cell and technique for measuring the scattered light intensities from small particles and molecules in solution over a broad range of scattering angles including those near zero degrees, it will be apparent to those of ordinary skill in the art of light scattering that many modifications and variations may be made therefrom without departing from the true spirit and scope of the invention. All such variations and modifications, therefore, are considered to be a part of the invention.

What is claimed is:

1. A sample cell for measuring the light scattering properties of a liquid suspension of particles at a plurality of scattering angles, where said liquid suspension of particles is illuminated by a light beam, comprising
   (a) optically polished sample channel means by which said suspended particles may be transported in a direction essentially parallel to said light beam through said sample cell;
   (b) light beam entrance and exit means sealed against said sample channel means and providing windows for said light beam to enter and exit said sample channel means without contacting walls of said sample channel means during passage through the sample cell;
   (c) scattered light transfer and refraction means of refractive index greater than said liquid sample and surrounding said liquid so that some light scattered by particles in said liquid may enter said refraction means;
   (d) optically polished external surface means surrounding said refraction means whereby some of the light scattered by the sample that has been refracted into said refraction means will exit said surface essentially normal to it and provide, thereby, a signal that may be detected by external detector means collimated to accept light passing through said surface at said detector location and essentially passing in a direction normal to said external surface; and
   (e) liquid transport means comprised of channels external and essentially normal to said illuminated sample channel through which liquid samples may be introduced to and removed from said illuminated sample channel.

2. The sample cell of claim 1 where the external surface means is a right cylinder.

3. The sample cell of claim 1 where the external surface means is a sphere.

4. The sample cell of claim 1 where the external surface means is a polyhedron.

5. The sample cell of claim 3 where the spherical cell is fabricated from two optically polished hemispheres each including part of a sample introduction channel; said hemispheres and matching channel elements being joined by index matching cement.

6. The sample cell of claim 5 where said each sample introduction channel of each hemisphere includes a hemispherical cavity concentric with said hemisphere.

7. A method for measuring the light scattering properties at a plurality of scattering angles of a aliquot of liquid-entrained particles comprising the steps of
   (a) preparing a transparent solid of refractive index greater than said liquid having two distinct optically finished surfaces:
      (i) a sample channel through said solid, and
      (ii) an external surface through which scattered light refracted from the liquid into the solid may be observed
   (b) filling said sample channel with the liquid sample whose light scattering properties are to be measured;
   (c) passing a fine light beam whose diameter is less than the sample channel diameter through the center of said sample channel and parallel to it so that no part of the incident beam will strike the liquid-solid interface;
   (d) sealing the ends of said sample channel with windows through which said fine light beam may enter and leave said sample channel essentially undeviated;
   (e) surrounding said external surface with a plurality of detectors all collimated so as to accept scattered light refracted by said transparent solid and leaving said external surface essentially normal to it.

8. The method of claim 7 where the transparent solid is glass.

9. The method of claim 7 where the external surface is that of a right circular cylinder and the internal sample channel lies along a diameter.

10. The method of claim 7 where the external surface is that of a sphere and the internal sample channel lies along a diameter.

11. The method of claim 7 where the external surface is that of a polyhedron.

12. The method of claim 10 where the internal sample channel intersects a central spherical cavity concentric with the external spherical surface.

13. The method of claim 7 where the fine light beam is from a laser.

14. The method of claim 7 where the laser is polarized.

15. The method of claim 7 where said plurality of detector surrounded said external surface are placed at angles $\theta_i'$ where $$\theta_i' = \cos^{-1}[(n_1/n_2)(1 - 2\sin^2\theta_i/2)],$$

$n_1$ = refractive index of the liquid,
$n_t$ = refractive index of the transparent solid, and
the scattering angles, $\theta_i$, are values selected equidistant in $\sin\theta/2$.

16. The method of claim 15 where the angles $\theta_i$ are chosen equidistant in $\sin\theta/2$ and $$0.2 \leq \sin\theta_i/2 \leq 0.9$$

in intervals of 0.05.

17. A method for attenuating the detected light scattered by larger liquid-entrained particles at small scattering angles comprising the steps of
   (a) preparing a transparent solid of refractive index greater than said liquid having two distinct optically finished surfaces:
      (i) a sample channel through said solid, and
      (ii) an external surface through which scattered light refracted from the liquid into the solid may be observed (b) filling said sample channel with the liquid sample whose light scattering properties are to be measured;

(c) passing a fine light beam whose diameter is less than the sample channel diameter through the center of said sample channel and parallel to it so that no part of the incident beam will strike the liquid-solid interface;

(d) detecting refracted scattered light by detector means located near said external surface at small transformed scattering angles.

18. The method of claim 17 where the refracted scattered light intensity is decreased as a function of scattering angle by the fraction $$1 = \rho_w = 1 - (\sin^2(\theta' - \theta)/\sin^2(\theta' + \theta)),$$

where $N_2 \cos 0' = \cos 0$, w is the fraction of light reflected at the liquid-transparent solid interface and $n_1$ and $n_2$ are the refractive indices of the liquid and transpaent solid, respectively.

19. The method of claim 17 where the transparent solid is glass.

20. The method of claim 17 where the external surface is that of a right circular cylinder and the internal channel lies along a diameter.

* * * * *

UNITED STATES PATENT AND TRADEMARK OFFICE
CERTIFICATE OF CORRECTION

PATENT NO. : 4,616,927

DATED : October 14, 1986

INVENTOR(S) : Steven D. Phillips et al

It is certified that error appears in the above-identified patent and that said Letters Patent is hereby corrected as shown below:

Column 4, line 38, "same" should read -- sample --.

Column 5, line 2, the symbol "$\theta$" should have a prime on it, i.e. should read -- $\theta'$ --

Column 5, line 36, "date" should read -- data --.

Column 8, line 40, the factor "(1-f)" should read -- (1-F) --.

Signed and Sealed this

Seventeenth Day of March, 1987

Attest:

DONALD J. QUIGG

*Attesting Officer*      *Commissioner of Patents and Trademarks*

UNITED STATES PATENT AND TRADEMARK OFFICE
CERTIFICATE OF CORRECTION

PATENT NO. : 4,616,927
DATED     : Oct. 14, 1986
INVENTOR(S) : Steven D. Phillips, et al.

It is certified that error appears in the above-identified patent and that said Letters Patent is hereby corrected as shown below:

Column 6, line 50 should read:

$$\rho_\omega = \frac{\tan^2(\theta'-\theta)}{\tan^2(\theta'+\theta)}$$

Column 12, lines 5 and 6 should read:

$$1-\rho_\omega = 1 - \tan^2(\theta'-\theta)/\tan^2(\theta'+\theta)$$

where $n_2 \cos\theta' = n_1 \cos\theta$, $\rho_\omega$ is the fraction of light re -

Column 12, line 9:

the word "transpaent" should be "transparent"

Column 8, line 63:

after the word "intensity insert "at the external source monitor"

Signed and Sealed this

Twenty-fifth Day of August, 1987

*Attest:*

DONALD J. QUIGG

*Attesting Officer*  *Commissioner of Patents and Trademarks*